United States Patent [19]
Tsyb et al.

[11] Patent Number: 5,314,400
[45] Date of Patent: May 24, 1994

[54] DEVICE FOR MAGNOTHERAPY

[76] Inventors: Anatoly F. Tsyb, prospekt Lenina, 4/3, kv. 26., Kaluzhskaya oblast, Obninsk; Pavel V. Sergeev, Truzhennikov pereulok, 19, kv. 19., Moscow; Vladimir I. Sharlai, prospekt Marxa, 8, kv. III., Kaluzhskaya oblast, Obninsk; Vladimir S. Dikun, ulitsa Golodeda, 39, korpus 3, kv. 27.; Nikolai S. Sobchuk, ulitsa Miroshnichenko, 49, kv. 16., both of Minsk; Tatyana N. Raiskaya, prospekt Marxa, 34, kv. 2II., Kaluzhskaya oblast, Obninsk; Anatoly D. Kotlyar, poselok Sosny, 8, kv. 33., Minsk; Vladimir M. Bolshov, ulitsa Marshala Timoshenko, 4, kv. 44., Moscow; Valery M. Tsarenkov, ulitsa Zaslavskogo, II, korpus 2, kv. 58.; Ljudmila V. Suloeva, ulitsa Olshevskogo, 23, kv. 57., both of Minsk; Oleg G. Bogatov, ulitsa Novaya, 5, kv. 138., Moskovskaya oblast, Zheleznodorozhny, all of U.S.S.R.

[21] Appl. No.: 31,933

[22] Filed: Mar. 15, 1993

Related U.S. Application Data

[63] Continuation of Ser. No. 935,477, Aug. 25, 1992, abandoned, which is a continuation of Ser. No. 449,877, Dec. 27, 1989, abandoned.

[30] Foreign Application Priority Data

Apr. 25, 1988 [SU] U.S.S.R. .............. 4408261[I]

[51] Int. Cl.$^5$ .............................................. A61N 2/00
[52] U.S. Cl. .................................................. 600/9; 600/14
[58] Field of Search ........................................ 600/9-15; 128/653.1

[56] References Cited

U.S. PATENT DOCUMENTS

| | | | |
|---|---|---|---|
| 4,315,503 | 2/1982 | Ryaby et al. | 600/14 |
| 4,428,366 | 1/1984 | Findl et al. | 600/14 |
| 4,723,536 | 2/1988 | Rauscher et al. | 600/14 |
| 4,911,668 | 3/1990 | Thaler | 600/14 |

FOREIGN PATENT DOCUMENTS

| | | | |
|---|---|---|---|
| 252197 | 11/1988 | Czechoslovakia . | |
| 0048451 | 3/1982 | European Pat. Off. . | |
| 0244046 | 11/1987 | European Pat. Off. . | |
| 2370483 | 7/1978 | France | 600/14 |
| 2546758 | 12/1984 | France . | |
| 697131 | 11/1979 | U.S.S.R. . | |
| 1273112 | 11/1986 | U.S.S.R. . | |
| 1321426 | 7/1987 | U.S.S.R. . | |

OTHER PUBLICATIONS

Stedman's Medical Dictionary, Williams and Wilkens, 24th edition, 1982.

*Primary Examiner*—Lee S. Cohen
*Assistant Examiner*—Krista M. Pfaffle
*Attorney, Agent, or Firm*—Burgess, Ryan & Wayne

[57] ABSTRACT

The invention relates to medicine and veterinary. The device for magnetotherapy comprises a variable generator (1) of current pulses, an energy accumulator (2) and a circuit (3) for discharge of the energy accumulator (2), including a controlled switching element (5) and an inductor (4) capable of producing a therapeutic pulsed magnetic field, and also a unit (7) for controlling the duration of pulses of the magnetic field produced by the inductor (4) and a controller (10) of the amplitude of pulses of the magnetic field. According to the invention, the discharge circuit (3) of the energy accumulator (2) includes a unit (6) for controlling the slope of the leading edge of pulses of the magnetic field produced by the inductor (4). The device is predominantly intended for arresting and relieving acute pain syndromes, phantom limb pain and attacks of bronchial asthma, and also for treating mastities of cattle.

7 Claims, 5 Drawing Sheets

DEVICE FOR MAGNOTHERAPY

This application is a continuation of application Ser. No. 935,477, filed Aug. 25, 1992, now abandoned, which is a continuation of application Ser. No. 449,877, filed Dec. 27, 1989, now abandoned.

FIELD OF THE INVENTION

The present invention relates to treatment of diseases, and more particularly it relates to a device for magnetotherapy.

BACKGROUND OF THE INVENTION

There is known a device for magnetotherapy, comprising a series connection of a generator of current pulses, an energy accumulator and an accumulator discharge circuit including a controlled switching element and an inductor capable of producing a therapeutic pulsed magnetic field. The device further comprises a unit for controlling the duration of pulses of the magnetic field produced by the inductor, having its output connected to the input of the controlled switching element (SU, A, 1321426).

The known device is intended for relieving the pain in the cases of radiculitis, plexitis and other diseases, and also for controlling the progress of X-ray contrast media in the organism of a patient. In the operation of the known device, the physician selects the patient-dependent amplitude and duration of pulses of the therapeutic magnetic field produced by the inductor, and also the quantity of sessions of treating the patient with the magnetic field. In this, the time required for selecting the parameters of magnetic pulses optimized for the patient in question is typically at least 3 to 7 minutes. Furthermore, as a magnetotherapy session is in progress, the eventually varying characteristics of the units of the device, e.g. on account of their heating, may cause leaps of the amplitude of pulses of the magnetic field produced, the leaps exceeding the permissible value not being positively precluded.

There is further known a device for magnetotherapy, comprising a series connection of a variable generator of current pulses, an energy accumulator and a discharge circuit of the energy accumulator, including a controlled switching element and an inductor capable of producing a therapeutic pulsed magnetic field, and also a unit for controlling the duration of pulses of the magnetic field produced by the inductor, having its output connected to the control input of the switching element, and a controller of the amplitude of pulses of the magnetic field, having its output connected to the input of the generator of current pulses (EP, B, 0048451). The amplitude controller of this device limits the peak values of the amplitude of pulses of the magnetic field. However, the selection of patient-optimized parameters of pulses of the therapeutic magnetic field in operation of this device is performed by way of time-consuming variation of the amplitude and duration of pulses, which, apart from being time-consuming, is not always adequately effective. Thus, this device has been found to be poorly manageable in the selection of the optimized parameters for relieving an acute pain syndrome, phantom limb pains, bronchial asthma attacks.

SUMMARY OF THE INVENTION

It is an object of the present invention to solve the problem of improving a device for magnetotherapy in a manner that it should comprise means for selecting the parameters and shape of pulses of the therapeutic magnetic field, providing for relieving an acute pain syndrome, phantom limb pains and bronchial asthma attacks of a given patient in the shortest time possible.

This object is attained in a device for magnetotherapy, comprising a series connection of a variable generator of current pulses, an energy accumulator and a discharge circuit of the energy accumulator, including a controlled switching element and an inductor capable of producing a therapeutic pulsed magnetic field, and also a unit for controlling the duration of pulses of the magnetic field produced by the inductor, having its output connected to the control input of the switching element, and a controller of the amplitude of pulses of the magnetic field, having its output connected to the control input of the generator of current pulses, in which device, in accordance with the present invention, the discharge circuit of the energy accumulator includes a unit for controlling the slope of the leading edge of pulses of the magnetic field produced by the inductor.

The unit for controlling the slope of the leading edge of the magnetic field pulses is optionally included between the output of the energy accumulator and the input of the switching element, and comprises at least two LC-circuits having their similar first ends joined, and a multiway switch having its fixed contacts connected to the respective other ends of the LC-circuits.

In an embodiment of the device in accordance with the present invention, wherein the inductor includes a multiple-turn inductance coil, it is expedient that the unit for controlling the slope of the leading edge of the magnetic field pulses should be structurally integrated with this coil, by having the winding of the coil provided with a plurality of taps lengthwise of the conductor, the coil being connected to the input of the switching element through a multiway switch having its fixed contacts connected each with the respective one of the taps.

To maintain permanence of the selected amplitude of magnetic field pulses as the slope of their leading edge is being varied, it is expedient that the device for magnetotherapy embodying the present invention should have its amplitude controller including a comparison circuit having its first input connected to the output of a sensor of the amplitude of pulses of the magnetic field, its second input connected to the output of a master control of the amplitude of pulses of the magnetic field, and its output connected to the output of the controller, the amplitude controller additionally including a memory unit between the output of the sensor of the amplitude of pulses of the magnetic field and the first inout of the comparison circuit, and a second comparison circuit having its first input connected with the output of the first comparison circuit, its second input connected to the output of the energy accumulator through a voltage divider, and its output connected to the output of the amplitude controller.

A device for magnetotherapy embodying the present invention, owing to its facility for selecting the optimized rise rate of the leading edge of pulses of the therapeutic magnetic field, provides for either relieving or arresting an acute pain syndrome, phantom limb pains, an attack of bronchial asthma within the first three minutes from the commencing of the effect. The employment of a device embodying the present invention provides for retaining the pain-relieving effect for 6 to 12 hours after the termination of a magnetotherapeutic sessions with the aid of the device.

BRIEF DESCRIPTION OF THE DRAWINGS

The invention will be further described in connection with its embodiments in a device for magnetotherapy, with reference being made to the accompanying drawings, wherein.

BEST MODE OF CARRYING OUT THE INVENTION

Figure 1:
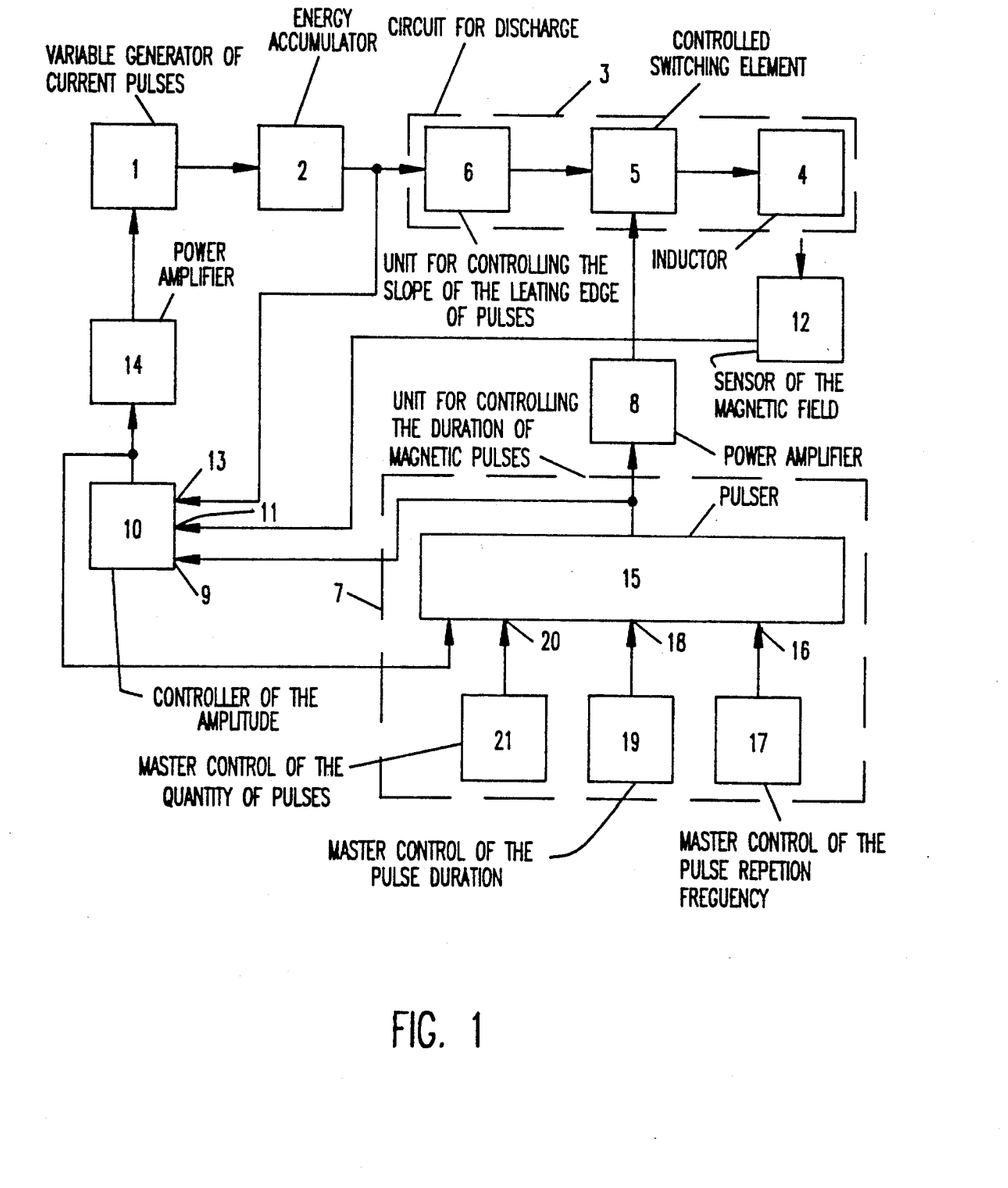
FIG. 1 is a block-unit diagram of a device for magnetotherapy, embodying the invention.

Referring now to the appended drawings, the device for magnetotherapy illustrated in FIG. 1 comprises a series connection of a variable generator 1 of current pulses, an energy accumulator 2 and a circuit 3 for discharge of the energy accumulator 2. The circuit 3 includes an inductor 4 and, connected to the input of the inductor 4 through a controlled switching element 5, a unit 6 for controlling the slope of the leading edge of pulses of the magnetic field produced by the inductor 4, the unit 6 having its input connected to the output of the energy accumulator 2. The device for magnetotherapy further comprises a unit 7 for controlling the duration of magnetic pulses, having its output connected through a power amplifier 8 to the control input of the switching element 5 and to the input 9 of the controller 10 of the amplitude of magnetic pulses, having another input 11 connected to the output of a sensor 12 of the magnetic field produced by the inductor 4 and yet another input 13 connected to the output of the energy accumulator 2, and its output connected through a power amplifier 14 to the control input of the generator 1 of current pulses. The unit 7 for controlling the duration of magnetic pulses comprises a pulser 15 with a variable frequency and duration of pulses, having its input 16 connected to a master control 17 of the pulse repetition frequency, its input 18 connected to a master control 19 of the pulse duration, its input 20 connected to a master control 21 of the quantity of pulses, and its control input connected to the output of the unit 10 for controlling the amplitude of magnetic pulses.

Figure 2:
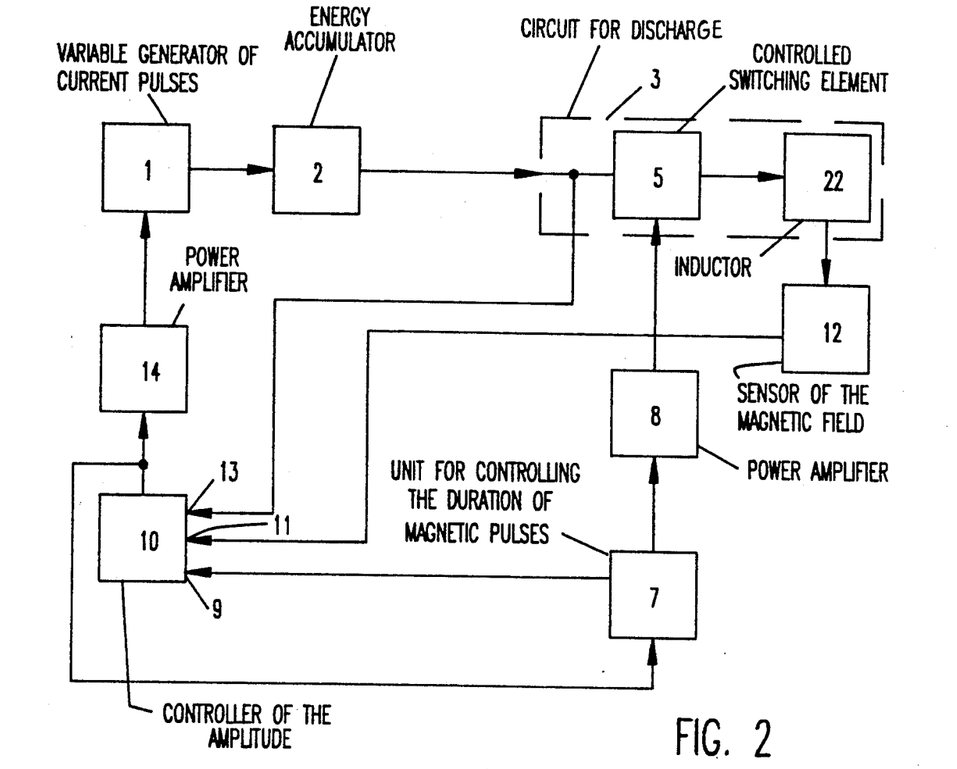
FIG. 2 is a block unit diagram of a modified embodiment of the device for magnetotherapy, wherein the inductor and the unit for controlling the slope of the leading edge of magnetic pulses are structurally integrated.

FIG. 2 of the appended drawings presents a block-unit diagram of a modified device for magnetotherapy, differing from the device of FIG. 1 in that its inductor 22 is structurally integrated with the unit for controlling the slope of the leading edge of magnetic pulses. In this embodiment, the discharge circuit 3 is devoid of a separate slope-controlling unit, and includes the inductor 22 having its input connected through the controlled switching element 5 directly to the output of the energy accumulator 2.

Figure 3:
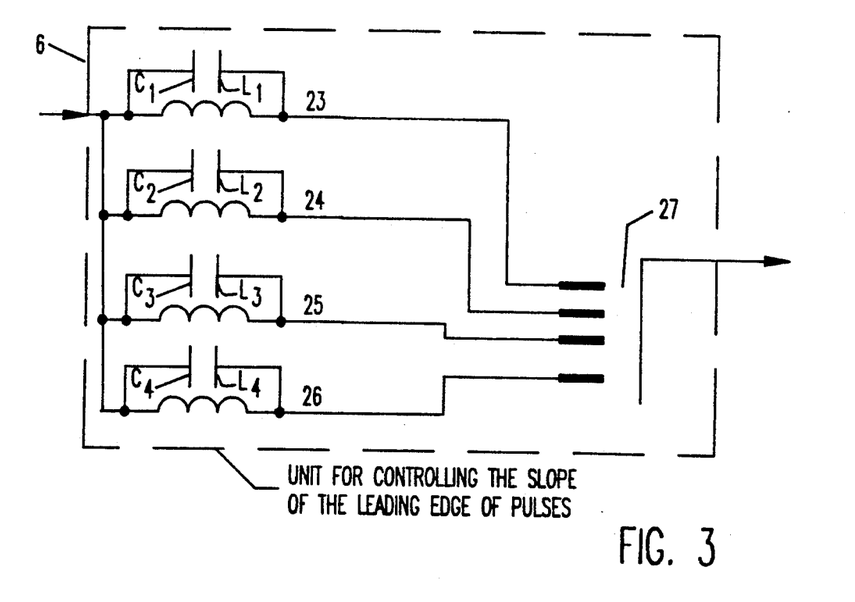
FIG. 3 is the circuit diagram of the unit for controlling the slope of the leading edge of magnetic pulses.

In the device for magnetotherapy of the embodiment of FIG. 1 the unit 6 for controlling the slope of the leading edge of magnetic pulses preferably has the circuitry illustrated in FIG. 3. In this modification, the unit 6 includes four parallel-connected LC-circuits 23, 24, 25 and 26 which generally have different values of L and C, having their inputs joined and connected to the output of the energy accumulator 2, and their outputs connected to the respective fixed contacts of a multiway selector switch 27 having its common movable contact connected to the input of the controlled switching element 5.

FIG. 3 illustrates a version of the unit 6 for controlling the slope of the leading edge of magnetic pulses, using a plurality of LC-circuits connected in parallel; however, the unit 6 may also have series-connected LC-circuits, or else a combination of parallel- and series-connected LC-circuits, provided this plurality allows to vary the equivalent L and C values of the unit 6 within the predetermined limits.

In a device for magnetotherapy, embodying the present invention, the inductor 4 may be in the form of a multiple-turn inductance coil capable of producing at the working surface of the inductor 4 a sufficiently uniform pulsed magnetic field of an intensity (strength) of about 200 kA/m, wherein kA/m = 1000 A/m. A/m is a measure of the intensity of a magnetic field in SI units wherein the conversion of SI units to CGS units is in accordance with the formula $$1 A/m = 4 \times 10^{-3} E.$$

Figure 4:
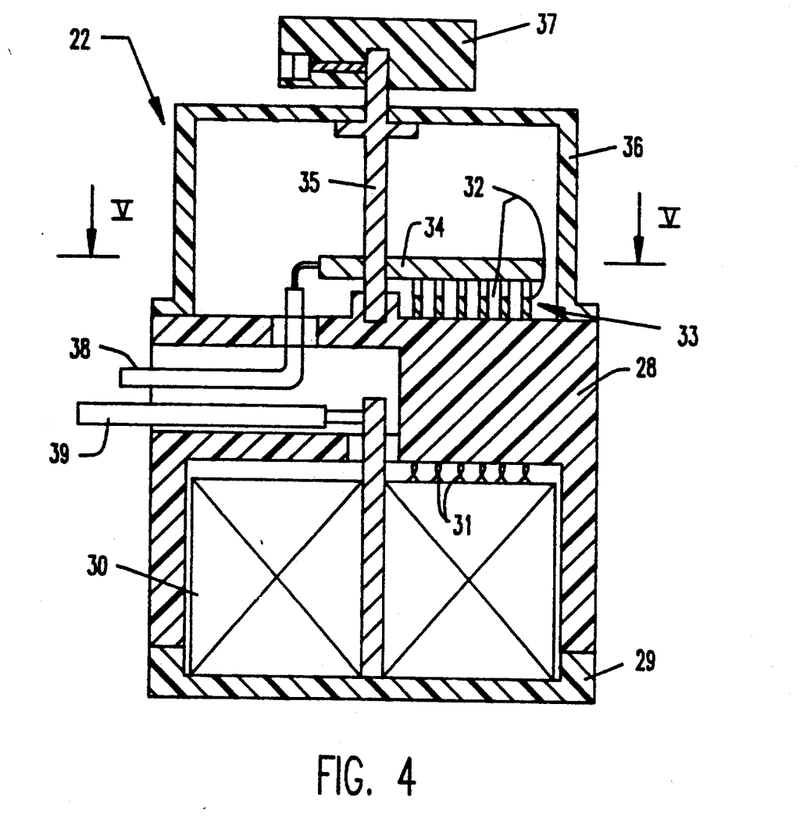
FIG. 4 is a schematic longitudinal sectional view of the inductor structurally integrated with the unit for controlling the slope of the leading edge of magnetic pulses.
Figure 5:
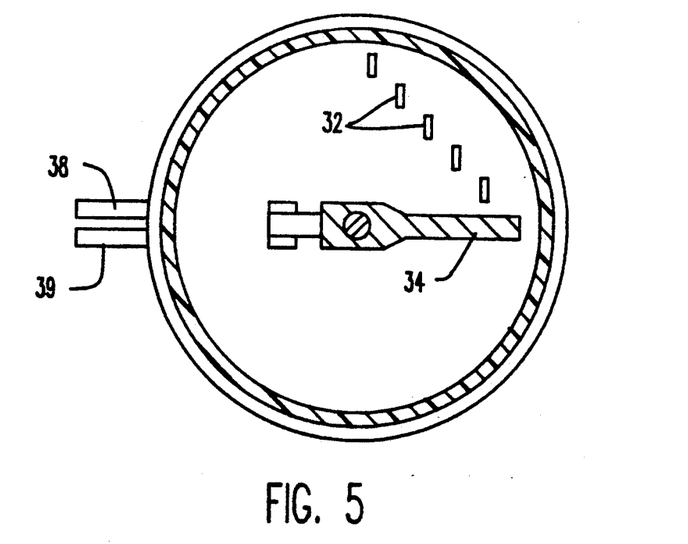
FIG. 5 is a sectional view taken on line V—V of FIG. 4.

FIGS. 4 and 5 illustrate schematically the inductor 22 in a modification structurally integrating the inductor as such and the unit for controlling the slope of the leading edge of magnetic pulses.

In this modification, the inductor 22 has a hollow cylindrical housing 28 of a dielectric material, provided with a removable cover 29. The housing 28 accommodates coaxially therein a helically strip-wound multiple-turn inductance coil 30 having a plurality—six in the version being described—of taps 31 lengthwise of its conductor. The taps 31 are electrically connected each with the respective fixed contact 32 of a multiway selector switch 33 of the commutator-strip type, whose common movable contact 34 is mounted on a central shaft 35 rotatably mounted in the housing 28. The selector switch 34 is protected by a cover 36 having mounted outside thereof a knob 37 secured on the end of the shaft 35 projecting beyond the cover 36, intended for turning the shaft 35 with the movable contact 34 through a selected angle. The movable common contact 34 is connected to a current lead 38, and one of the ends of the coil 30—its inner end in the version being described—is connected with a current lead 39. The current leads 38 and 39 extend outside the housing 28.

Figure 6:
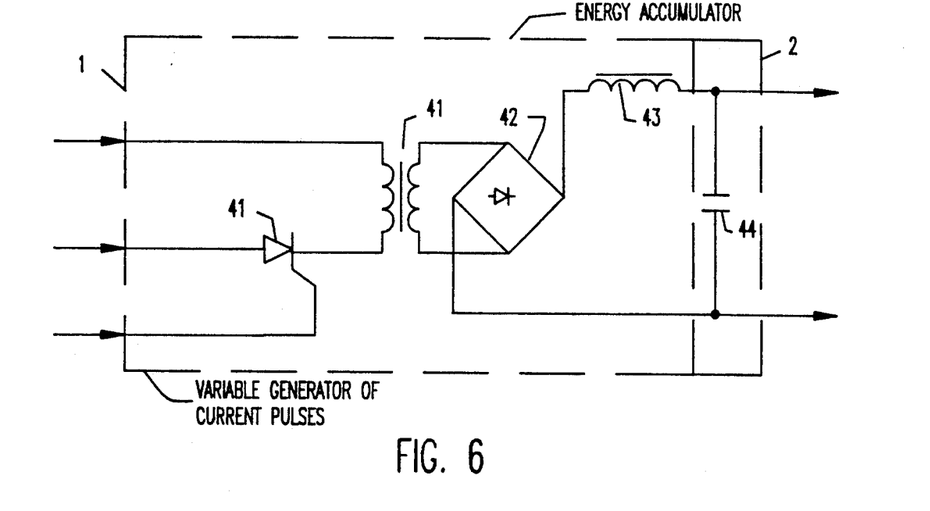
FIG. 6 is a circuit diagram of the generator of current pulses and energy accumulator.

FIG. 6 of the appended drawings present the circuit diagram of the generator 1 of current pulses with the energy accumulator 2. The generator 1 of current pulses includes a transformer 40, a gate-controlled semiconductor switch (of the Triac type) 41 serially connected in the circuit of the primary winding of the transformer 40 and having its control input serving as the control input of the generator 1 of current pulses connected to the power amplifier 14 and a rectifier diode bridge circuit 42 having its inputs connected to the secondary winding of the transformer 40. The output of the rectifying bridge circuit 42 has connected thereto in series a current-limiting choke 43 and the energy accumulator 2 including a capacitor bank 44 forming a charging circuit through which the charging current intermittently flows in operation of the device. The capacitor bank 44 preferably includes pulse capacitors with low inductance of their own.

The sensor 12 of pulses of the magnetic field is preferably in the form of a crystal-type Hall generator.

The power amplifiers 8 and 14 are preferably transistorized emitter followers.

The pulser 15 is preferably a widely known low-frequency pulser with microcircuitry hardware, wherein the variables of the frequency-defining LC-circuits are controlled by the signals coming from the master controls 19 and 17, respectively, of the pulse duration and repetition frequency, the master controls 19 and 17 themselves preferably being multiway selector switches.

The master control 21 of the quantity of pulses is preferably a multiway decade switch, the pulser 15 additionally including a pulse counter and a digital comparator, the switch 21 being connected to one group of the inputs of the digital comparator, and the pulse counter being connected to the other group of the inputs of this digital comparator (not shown in the drawings).

Figure 7:
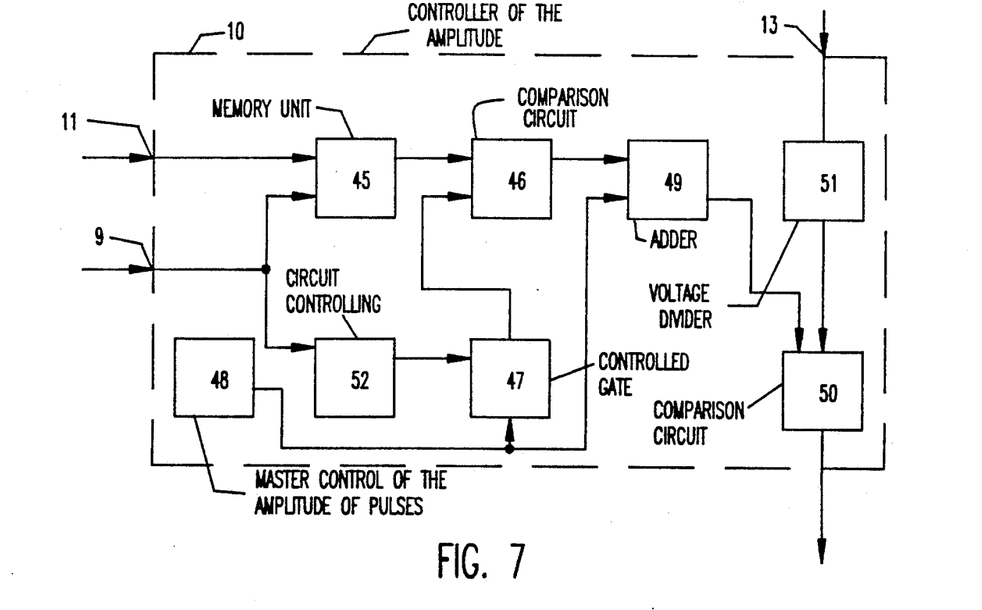
FIG. 7 is a block-unit diagram of the amplitude-controlling unit.

The controller 10 of the amplitude of pulses of the magnetic field, whose block-unit diagram is illustrated in FIG. 7, comprises a memory unit 45 having one input connected to the input 11 of the controller 10 and its other input connected to the input 9 of the same controller 10, a comparison circuit 46 having its first input connected to the output of the memory unit 45 and its other input connected through a controlled gate 47 to the output of a master control 48 of the amplitude of pulses of the magnetic field, an adder 49 having one input connected to the output of the comparison circuit 46 and its other input directly connected to the output of the master control 48 of the amplitude of pulses of the magnetic field, a comparison circuit 50 having its first input connected to the output of the adder 49, its other input connected through a voltage divider 51 to the input 13 of the controller 10, and its output serving as the output of the controller 10 of the amplitude of pulses of the magnetic field, and a circuit 52 controlling the gate 47, its input being connected to the input 9 of the controller 10 and its output being connected to the control input of the controlled gate 47. The components 45, 46, 49 and 50 are built about commonly known operational amplifiers, and the amplitude master control 48 is preferably a voltage divider incorporating a variable resistor.

The circuit 52 controlling the gate 47 is preferably a set-reset (R-S) flip-flop.

The device for magnetotherapy is operated, as follows.

Prior to connecting the device to the power supply, the master controls 17 (FIG. 1), 19, 21, respectively, of the repetition frequency, duration and quantity of pulses, the master control 48 (FIG. 7) of the amplitude of pulses of the magnetic field of the amplitude controller 10, and the multiway selector switch 27 (FIG. 3) are set an operating condition of the device for magnetic therapy, which has proved to be most effective in the treatment of the majority of patients with a given pathology, i.e. the operating physician presents tentatively the repetition frequency, duration, amplitude, slope of the leading edge of magnetic field pulses and their quantity for the forthcoming treatment session. The inductor 4 (FIG. 1) jointly with the sensor 12 of the amplitude of pulses of the magnetic field built into the base of the cylindrical inductor 4, intended to face the object to be treated, is set in the area of the intended therapeutic effect so that the working surface of the abovementioned base of the inductor 4 (the face of the inductance coil) should either directly engage the patient's body or be brought very close thereto. When the voltage from the power mains is supplied to the power input of the device for magnetotherapy, the capacitor bank 44 (FIG. 6) of the energy accumulator is being charged, as the gate-controlled switch 41 is initially open, and the charging current flows through the primary winding of the transformer 40, inducing a.c. voltage in its secondary winding, which is converted into d.c. voltage by the rectifying diode bridge circuit 42. The choke 43 keeps the charging current within the predetermined limits. The information of the voltage value across the energy accumulator 2 is sent by its output to the input 13 (FIG. 1) of the pulse amplitude controller 10. As the energy accumulator 2 builds up its stored voltage to a value sufficient for producing a magnetic field pulse of the amplitude preset with the amplitude master control 48 (FIG. 7), the amplitude controller sends out a signal closing the gate-controlled switch 41 (FIG. 6), thus terminating the charging of the energy accumulator 2. The latter is thus prepared for a discharge. Simultaneously, the controller 10 (FIG. 1) sends from its output to the input of the pulser 15 a signal permitting the pulse duration control unit 7 to send a pulse to the control input of the switching element 5, whereby the switching element connects the discharge circuit 3 to the input of the energy accumulator 2, triggering a discharge of the energy accumulator 2 via the discharge circuit 3 including the slope control unit 6 in which the multiway selector switch 27 (FIG. 3) has been operated to include into the discharge circuit 3 one of the LC-circuits 23 to 26, e.g. the LC-circuit 23. With the LC-circuits 23-26 being switched over by the selector switch 27 in the unit 6, there are varied the equivalent values of resistance $R_o$, inductance $L_o$ and capacitance $C_o$ of the discharge circuit 3 (FIG. 1), defining the parameters of pulses of the magnetic field produced by the inductor 4, including the important parameter $\tau_f$, i.e. the rise rate of a magnetic pulse defining the slope of its leading edge.

Figure 8:
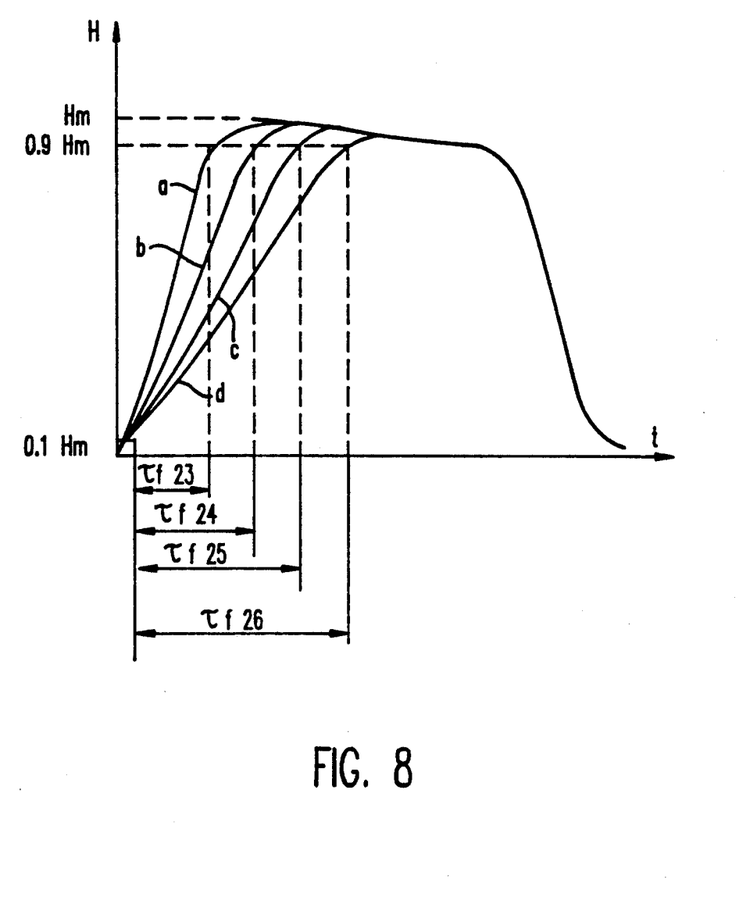
FIG. 8 presents curves illustrating variation of the intensity H of the magnetic field of the inductor vs. time t, with the y-axis being calibrated in the units of intensity H (kA/m) and X-axis being calibrated in units of time t (s).

FIG. 8 illustrates the shapes of pulses of the magnetic field produced by the inductor 4 (FIG. 1) for different versions of connection of the LC-circuits 23 to 26 (FIG. 3) in the slope control unit 6.

The curve "a" in FIG. 8 depicts the shape of a pulse when the switching element 5 (FIG. 1) has connected to it through the selector switch 27 (FIG. 3) the LC-circuit 23; the curve "b" shows the same for the LC-circuit 24, and the curves "c" and "d" show the same, respectively, for the LC-circuits 25 and 26.

As the slope of the leading edge of a pulse is defined by the ratio of its amplitude to the rise rate $\tau_f$, the variation of $\tau_f$ varies the slope of the leading edge of a pulse of the magnetic field, in which way the slope of the magnetic field pulses is controlled in the device for magnetotherapy being disclosed.

The controller 10 (FIG. 7) of the amplitude of magnetic pulses is operated, as follows.

With the device for magnetotherapy connected to the power supply mains and until the energy accumulator 2 (FIG. 1) sends out the first discharge pulse and the memory unit 45 (FIG. 7) stores the value of the actual amplitude of a magnetic field pulse from a signal coming from the sensor 12 (FIG. 1) of the magnetic field, the first comparison circuit 46 (FIG. 7) receives a "0" signal. The signal sent to the other input of the comparison circuit 46 is also "θ", as the signal from the master control 48 of the amplitude of pulses would not pass through the controlled gate 47 closed by the signal sent by the control circuit 52. Consequently, the comparison circuit 46 shapes a "0" output signal sent to one input of the adder 49, the other input of the adder 49 being fed the signal from the master control 48 of the amplitude of the magnetic field pulses. The adder 49 feeds out from its output a signal equalling the signal coming from the amplitude master control 48 to the comparison circuit 50, to be compared with the signal coming from the voltage divider 51 through the input 13 from the energy accumulator 2 (FIG. 1) and carrying the information on the voltage value across the accumulator 2.

When the signals coming to the two inputs of the comparison circuit 50 (FIG. 7) become equal, its output shapes a signal turning off through the amplifier 14 (FIG. 1) the gate-controlled semiconductor switch 41 (FIG. 6), to discontinue the charging of the capacitor bank 44 of the energy accumulator 2.

At the very same moment the control unit 7 (FIG. 1) sends a signal to the input 9 of the amplitude controller 10, fed subsequently to the input of the memory unit 45 (FIG. 7), preparing the latter to receive and store a pulse expected from the pulse amplitude sensor 12 (FIG. 1), and to the control circuit 52 (FIG. 7) to shape at its output a signal turning on (opening) the gate 47 via its control input. Thus, the gate 47 would be held open from the moment of the appearance of the first pulse until the moment when the device has produced the quantity of magnetic field pulses preset with the master control 21 (FIG. 1) of the unit 7, and then the units of the device are restored to the initial state. During the discharge of the energy accumulator 2 (i.e. during the pulse "on" time) the memory unit 45 (FIG. 7) stores the information coming from the amplitude sensor 12 (FIG. 1) and representing the actual value of the amplitude of the pulse of the magnetic field that has been produced by the inductor 4.

Thus, upon the production of the first magnetic field pulse, the respective inputs of the comparison circuit 46 (FIG. 7) are fed with the signal coming from the memory unit 45 and representing the actual value of the magnetic field pulse, and the signal from the master control 48 of the amplitude of pulses of the magnetic field, coming through the open gate 47 and representing the preset value of the amplitude. The comparison circuit 46 compares the value of the actual and preset amplitudes of the magnetic field pulse and feeds out a mismatch signal. The last-mentioned signal is fed to the first input of the adder 49 which, depending on the sign of the signal, alters (i.e. increases or decreases) the value of the signal coming from the amplitude master control 48 to the second input of the adder 49, the latter sending its output signal to the first input of the comparison circuit 50. This signal is, in fact, the signal predetermining the amplitude of the magnetic field pulse accounting for the correction of disturbances introduced into the discharge circuit 3 (FIG. 1), e.g. when the LC-circuits 23-26 (FIG. 3) are switched over in the unit 6. In this way the permanence of the amplitude of pulses of the magnetic field produced by the inductor 4 is maintained in accordance with the preset value. Thus, if the actual amplitude of a pulse of the magnetic field exceeds the preset value, the level of the signal coming to the respective input of the comparison circuit 50 becomes lower than that of the signal coming from the pulse amplitude master control 48. Consequently, the signal from the voltage divider 51 coming to the other input of the comparison circuit 50 levels out with the signal coming to its first input with a lower voltage stored by the energy accumulator 2 (FIG. 1). As the energy stored by the accumulator 2 thus becomes less, the amplitude of the successive pulse of the magnetic field when the accumulator 2 discharges through the discharge circuit 3 also becomes less, down to the preset value.

Then the abovedescribed operating cycle of the device is repeated. When the quantity of magnetic field pulses produced by the device for magnetotherapy reaches the amount preset with the master control 21, the operation of the device is discontinued, and it is restored to the initial state. The parameters of the charging circuit of the accumulator 2 are chosen so that the accumulator 2 should be able to become charged to the maximum specified voltage in operation at the maximum specified pulse repetition frequency.

The modification of the herein disclosed device for magnetotherapy, illustrated in FIG. 2, operates in a similar manner. The difference is that here the slope of the leading edge of a magnetic field pulse is controlled by varying the inductance of the inductor 22 itself. The varying parameters of the inductor 22 and the switching-over in the slope control unit 6 (FIG. 1) would alter the parameters of the discharge circuit 3, affecting also the amplitude of the magnetic field pulses. However, this variation would be responded to by the sensor 12 of the amplitude of the magnetic field, and the amplitude controller 10 would compensate for this variation in the abovedescribed way, maintaining the amplitude of the pulses of the magnetic field at its preset value $H_m$.

A device for magnetotherapy constructed in accordance with the present invention generates at the working surface of the inductor 4 (22) of the magnetic field successive magnetic field pulses of a duration $10^{-2} - 10^{-6}$ s, with an amplitude 500-2000 kA/m and repetition frequency from 0.25 to 2.0 Hz.

An advantage of the herein disclosed device is that it offers the possibility of dynamically controlling the therapeutic process. By adjusting the slope of the leading edge of the magnetic field pulses in the course of the treatment of a patient, this all-important parameter can be selected in accordance with the personal response of the patient's organism, so that the pain-relieving effect is attained within the optimally short time.

The herein disclosed device allows to vary the slope of the leading edge of the magnetic field pulses (the pulse rise rate) within a range from $5 \cdot 10^5$ to $2 \cdot 10^8$ kA/m·s.

The steeper slope of the leading edge of the magnetic field pulses and its adjustability provide for enhancing the therapeutic effect of the treatment; thus, in the treatment of lumbosacral radiculitis in a single session, the pain-relieving time can be reduced on the average 2.5 times, while the persistence of the pain-relieving effect is increased 4.5 times on the average.

The automatic stabilization of the magnetic field amplitude at a preset value eliminates the necessity of manual monitoring and stabilization of the amplitude of pulses of the magnetic field, which both simplify the procedure of conducting a magnetotherapeutic session and cuts its time.

A prototype of a device for magnetotherapy embodying the present invention has been manufactured and tested in the clinical environment.

The outcome of the testing is summarized hereinbelow.

The device for magnetotherapy embodying the invention was employed for relieving the acute posttraumatic pain in the areas of dissection of necrosis of a patient with purulent necrotic wounds of the crus. The amplitude of pulses of the therapeutic magnetic field was set at 1300 kA/m; the pulse duration, at $3 \cdot 10^{-4}$ s; and the pulse rise rate (the slope of the leading edge of the pulses), at $2 \cdot 6 \cdot 10^7$ kA/m·s. Upon having received 50 pulses (about 2.5 minutes), the patient experienced the subjective sensation of the absence of pain. Following a magnetotherapeutic session of 100 pulses, the analgetic effect was retained for 6 hours. After 5 sessions of 100 pulses, the wounds healed and the pain disappeared.

The device for magnetotherapy was also employed for relieving the phantom limb pain of a patient with the amputation stump of the left crus. The amplitude of the magnetic field pulses was set at 1500 kA/m; the pulse duration, at $3 \cdot 10^{-4}$ s, the pulse rise rate, at $7 \cdot 5 \cdot 10^7$ kA/m·s. Following the application of 55 pulses (about 2.7 minutes), the patient experienced the subjective sensation of the absence of pain. After the first magnetotherapeutic session of 70 pulses, the analgetic effect persisted for 2 hours; after the second session of 70 pulses, for 10.5 hours; and after the third session of 70 pulses, the phantom limb pain did not recur.

INDUSTRIAL APPLICABILITY

The invention can be successfully employed in medicine for treatment of human diseases accompanied by an acute pain syndrome, such as radiculitis, osteochondrosis, arthrosis, plexitis, for arresting an acute pain syndrome in the post-operation period, and also in veterinary for treating animals, e.g. for treating mastitis of cattle, in chemistry and biology.

We claim:

1. A magnetotherapy device comprising:
  a series connection of:
    variable generator means for providing current pulses,
    an energy accumulator, and
    discharge circuit means for discharging energy accumulated by the energy accumulator, said discharge circuit means including:
    a controlled switching element,
    inductor means for producing a therapeutic pulsed magnetic field containing pulses and having an input connected with said controlled switching element, and
    means for controlling slopes of leading edges of the pulses of the magnetic field produced by the inductor means,
  means for controlling the duration of the pulses of the magnetic field produced by the inductor means, the means for controlling the duration of the pulses having an output connected to a control input of the controlled switching element, and
  controller means for controlling amplitudes of the pulses of the magnetic field, and having an output connected to a control input of the variable generator means.

2. The device of claim 1 wherein said means for controlling the slopes of the magnetic field pulses is positioned between an output of the energy accumulator and an input of the controlled switching element and further comprises at least two LC-circuits connected in parallel and a multi-way selector switch having fixed contacts connected to one end of the LC-circuits.

3. A device of claim 2 wherein said inductor means comprises a multiple-turn inductance coil and wherein the means for controlling the slopes of the magnetic field pulses is structurally integrated with the inductor means, said inductance coil comprising a conductor having a plurality of taps lengthwise of the conductor, each of said taps being connected to said fixed contacts of the multi-way selector switch.

4. The device of claim 2 wherein the amplitude controller means comprises:
  a memory having an input which comprises a first input of said amplitude controller means, and an output;
  a first comparison circuit having a first input connected to said output of said memory, a second input, and an output;
  a pulse amplitude master control means for setting the amplitudes of the pulses and having an output electrically connected with said second input of said first comparison circuit;
  a second comparison circuit having a first input electrically connected with said output of said first comparison circuit, a second input and an output which comprises an output of said amplitude controller means; and
  a voltage divider having an input which comprises a second input of said amplitude controller means and an output connected to said second input of said second comparison circuit.

5. The device of claim 1 wherein said means for controlling includes a multi-way selector switch and said inductor means comprises a multiple-turn inductance coil and wherein the means for controlling the slopes of the magnetic field pulses is structurally integrated with the inductor means, said inductance coil comprising a conductor having a plurality of taps lengthwise of the conductor, each of said taps being connected to fixed contacts of said multi-way selector switch.

6. The device of claim 5 wherein the amplitude controller means comprises:
  a memory having an input which comprises a first input of said amplitude controller means, and an output;
  a first comparison circuit having a first input connected to said output of said memory, a second input, and an output;
  a pulse amplitude master control means for setting amplitudes of the pulses and having an output electrically connected with said second input of said first comparison circuit;
  a second comparison circuit having a first input electrically connected with said output of said first comparison circuit, a second input and an output which comprises an output of said amplitude controller means; and a voltage divider having an input which comprises a second input of said amplitude controller means and an output connected to said second input of said second comparison circuit.

7. The device of claim 1 wherein the amplitude controller means comprises:
- a memory having an input which comprises a first input of said amplitude controller means, and an output;
- a first comparison circuit having a first input connected to said output of said memory, a second input, and an output;
- a pulse amplitude master control means for setting the amplitudes of the pulses and having an output electrically connected with said second input of said first comparison circuit;
- a second comparison circuit having a first input electrically connected with said output of said first comparison circuit, a second input and an output which comprises an output of said amplitude controller means; and
- a voltage divider having an input which comprises a second input of said amplitude controller means and an output connected to said second input of said second comparison circuit.

* * * * *